United States Patent [19]

Lund

[11] Patent Number: 4,679,448
[45] Date of Patent: Jul. 14, 1987

[54] SYSTEM FOR THE INTERNAL INSPECTION OF PIPELINES

[75] Inventor: Svend Lund, Birkerod, Denmark

[73] Assignee: Akademiet for de Tekniske Videnskaber, Svejsecentralen, Glostrup, Denmark

[21] Appl. No.: 721,678

[22] Filed: Apr. 10, 1985

[51] Int. Cl.$^4$ .......................................... G01M 19/00
[52] U.S. Cl. ................................................ 73/866.5
[58] Field of Search ............ 73/432 G, 40.5 R, 432 B, 73/432 R, 623; 350/96.23, 96.26; 33/125 B, 302, 1 H, 141, G, 529; 104/138 G, 138 R, 297, 287, 154, 295, 296, 155, 156; 105/365; 378/60; 358/100, 98, 107; 324/220

[56] References Cited

U.S. PATENT DOCUMENTS

| | | | |
|---|---|---|---|
| 2,940,302 | 6/1960 | Scherbatskoy | 324/220 X |
| 3,718,978 | 3/1973 | Vankoevering et al. | 104/138 G X |
| 4,473,841 | 9/1984 | Murakoshi et al. | 358/98 |
| 4,560,931 | 12/1985 | Murakami et al. | 73/623 X |
| 4,572,228 | 2/1986 | Larson et al. | 73/40.5 R X |
| 4,586,079 | 4/1986 | Cooper, Jr. et al. | 358/100 |

FOREIGN PATENT DOCUMENTS

| | | | |
|---|---|---|---|
| 670410 | 9/1963 | Canada | 138/97 |
| 135820 | 10/1981 | Japan | 350/96.26 |
| 198419 | 12/1982 | Japan | 350/96.23 |
| 26256 | 2/1983 | Japan | 324/220 |
| 137806 | 8/1983 | Japan | 350/96.23 |
| 7510608 | 9/1974 | Netherlands | 73/432 B |

Primary Examiner—Stewart J. Levy
Assistant Examiner—Tom Noland
Attorney, Agent, or Firm—Banner, Birch, McKie & Beckett

[57] ABSTRACT

A system for the internal inspection of pipelines for carrying oil or gas, subsea or overland, includes an apparatus carrier, pressure-driven driven or self-propelled, carrying non-destructive examination apparatus moved through the pipeline to inspect the safety conditions of the pipeline wall material and surfaces. During its progression the carrier gradually deposits one or more expendable, thin optical fibers inside the pipeline. The fibers connect the carrier with a control station, situated outside the pipeline at the carrier launching end of the pipeline, through electro-optical signal converters installed in the carrier and in the control station. The system permits continuous on-line communication with the carrier over very long distances (1) for generating instant visual displays and permanent records of the step-by-step results of the inspection, (2) for controlling the functions of the non-destructive examination apparatus, and (3) for controlling the rate of progression of the carrier. Upon completion of the inspection the optical fibers are discarded inside the pipeline for later removal, if necessary, by a routine in-service cleaning operation.

4 Claims, 2 Drawing Figures

SYSTEM FOR THE INTERNAL INSPECTION OF PIPELINES

BACKGROUND OF THE INVENTION

1. Field of the Invention

This invention relates to the internal inspection of pipelines for carrying fluids, such as oil or gas, over considerable distance, subsea or overland, between accessible ends of individual pipeline sections. Pipelines of this kind which are normally inaccessible from the outside must be inspected at regular intervals from the inside for possible corrosion attacks, cracking, or other defects, in order to prevent costly production interruptions, catastrophic failure, and/or disasterous severances of the supply of energy to the community.

2. Background of the Prior Art

For such internal inspections, a great variety of apparatus carriers, pressure-driven "pigs" or self-propelled "crawlers," have been developed and used for carrying visual, magnetic, electric, ultrasonic or similar non-destructive examination apparatus through a pipeline from a launching trap at one end to a receiving trap at the other end of a pipeline section. Typically, such apparatus carriers may contain pressure-tight capsules for non-destructive examination apparatus, position determining apparatus, recording means, driving mechanisms, and battery or turbo-generator units for energizing the various apparatus in the carrier. After the passage of the apparatus carrier, the recording means may then be removed and connected to display and record means situated outside the pipeline for analysis, evaluation, and permanent recording of the results of the inspection. An extensive description of an inspection system of this kind has been given in Scherbatskoy U.S. Pat. No. 2,940,302.

It is a severe drawback of most known inspection systems of this kind that it is impossible to communicate with the apparatus carrier during its passage through the pipeline for obtaining instant on-line displays of the results of the inspection, and for controlling the functions of the non-destructive examination apparatus and the rates of progression of the apparatus carrier.

For relatively short pipeline sections, such as offshore platform oil or gas risers, it is possible to use cable connected apparatus carriers communicating on-line with outside display, recording and control means. This requires, however, the very costly operations of interrupting production and emptying the pipeline section in question. For pipeline sections of more than a few hundred meters in length, the use and recovery of electric cables becomes impractical. An example of a system of this kind, using a cable connected apparatus carrier containing television and leak testing apparatus has been described in Cramer U.S. Pat. No. 3,400,574.

It has been proposed in the above-mentioned Scherbatskoy U.S. Pat. No. 2,940,302 to use the pipeline as a dielectric wave guide for the wireless transmission of acoustic or microwave signals between the apparatus carrier and an outside recording and control station. This system has, however, been found inapplicable due to antenna and transmission problems, and it has not found use in actual practice.

SUMMARY OF THE INVENTION

The system according to the present invention has been evolved with the general object of overcoming the disadvantages of prior systems and providing a system for the internal inspection of a pipeline in which it has become possible to obtain continuous on-line communication over considerable distances between a control station situated outside the pipeline and an apparatus carrier during the progression of the carrier through an entire pipeline section to be examined.

According to the invention this communication possibility is obtained through the use of one or more expendable, thin optical fibers connected and adapted to transmit optical measurement and control signals between the carrier and an outside control station. One or more coils of optical fibers having at least the same length as the pipeline section are mounted on the apparatus carrier, and the fibers are gradually deposited inside the pipeline during the progression of the carrier. Upon completion of the inspection, the optical fibers are discarded inside the pipeline or, if it should be considered necessary, removed by a subsequent routine in-service cleaning operation. This important feature of using expendable optical fibers has become practically and economically feasible through the present-day mass production of single optical fibers of continuous lengths of up to 50 km or more.

The optical fibers are connected at both ends to conventional electro-optical signal converters mounted in the apparatus carrier and in the outside control station, respectively, and adapted to convert electronic measurement and control signals into corresponding optical signals, and to convert such optical signals back into equivalent electronic signals. Electro-optical signal converters of this kind may, in principle, be installed and connected in any inspection apparatus carrier known in the state of the art, and in any known corresponding display, recording or control means situated outside the carrier launching end of the pipeline section to be examined.

One important object of the invention is to make it possible to transmit measurement signals from the non-destructive examination apparatus and from the position determining apparatus mounted in the apparatus carrier to an outside control station for producing instant on-line visual displays of the step-by-step conditions of the pipeline wall material and surfaces, and permanent recordings of the results of the inspection.

Another important object of the invention is to make it possible to transmit control signals from outside control means to the apparatus carrier for obtaining step-by-step on-line control of the functions of the non-destructive examination apparatus installed in the apparatus carrier. Such control may comprise on/off switching of the various apparatus, directing and focusing of television cameras and corresponding illuminating systems, changing between different examination probes and scanning patterns, and several similiar controlling operations as required.

Still another important object of the invention is to make it possible to transmit control signals from outside control means to a self-propelled apparatus carrier for obtaining step-by-step on-line control of the functions of the driving mechanisms of the apparatus carrier. Such control may comprise on/off switching, control of battery or turbo-generator energizing systems, control of direction and rate of progress of the carrier for closer inspection of suspicious-looking areas of the pipeline wall, and similar control operations as required.

DETAILED DESCRIPTION OF THE ILLUSTRATED EMBODIMENT

Figure 1:
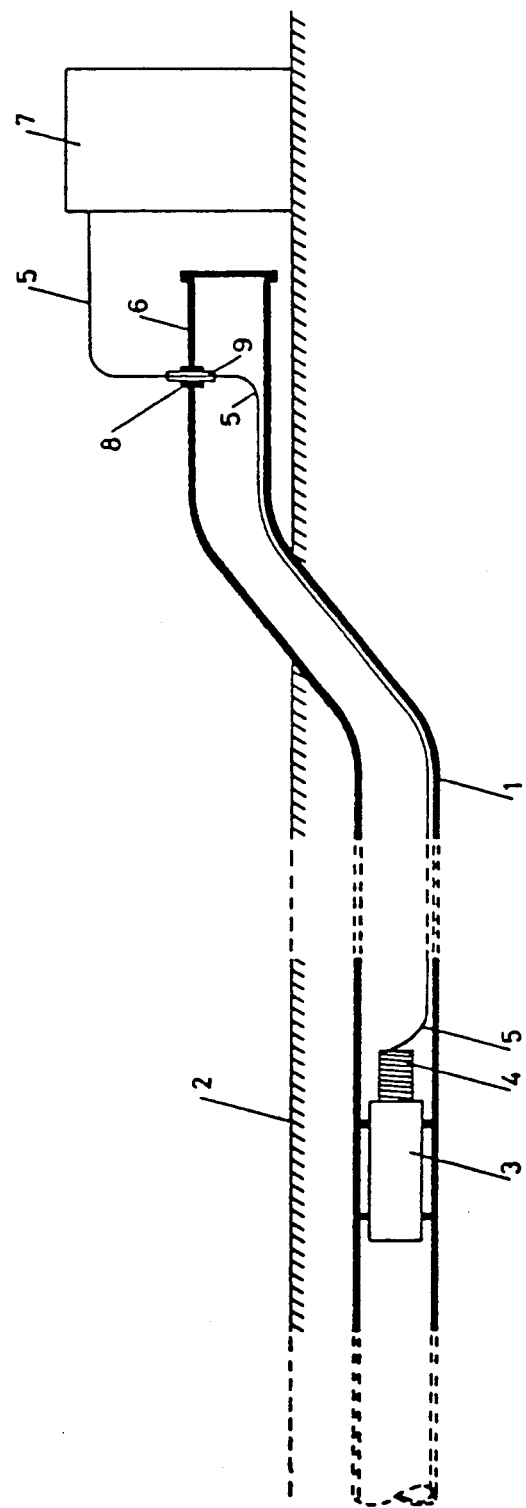
FIG. 1 is a schematic view of a system according to the invention for the internal inspection of a pipeline.

FIG. 1 shows schematically part of a section of a pipeline 1 for carrying fluids, such as oil or gas. The main part of the pipeline is buried below the earth's surface 2 and is thus normally inaccessible from the outside. An apparatus carrier 3 is inserted in one end 6 of the section of pipeline 1. The apparatus carrier 3 is adapted to travel inside the pipeline from point to point until it reaches the other end of the pipeline section.

A coil 4 of expendable, thin optical fiber 5, having at least the same length as the section of the pipeline to be inspected is mounted on the apparatus carrier 3. The coil 4 is adapted to gradually deposit the optical fiber 5 during the progression of the carrier 3 through the pipeline 1. The optical fiber 5 connects the apparatus carrier 3 with an outside control station 7 situated at the carrier launching end 6 of the pipeline 1. A bushing 8 is fitted into the wall of the pipeline at the carrier launching end 6 and adapted to receive a pressure-tight lead-in plug 9 for the optical fiber 5.

Figure 2:
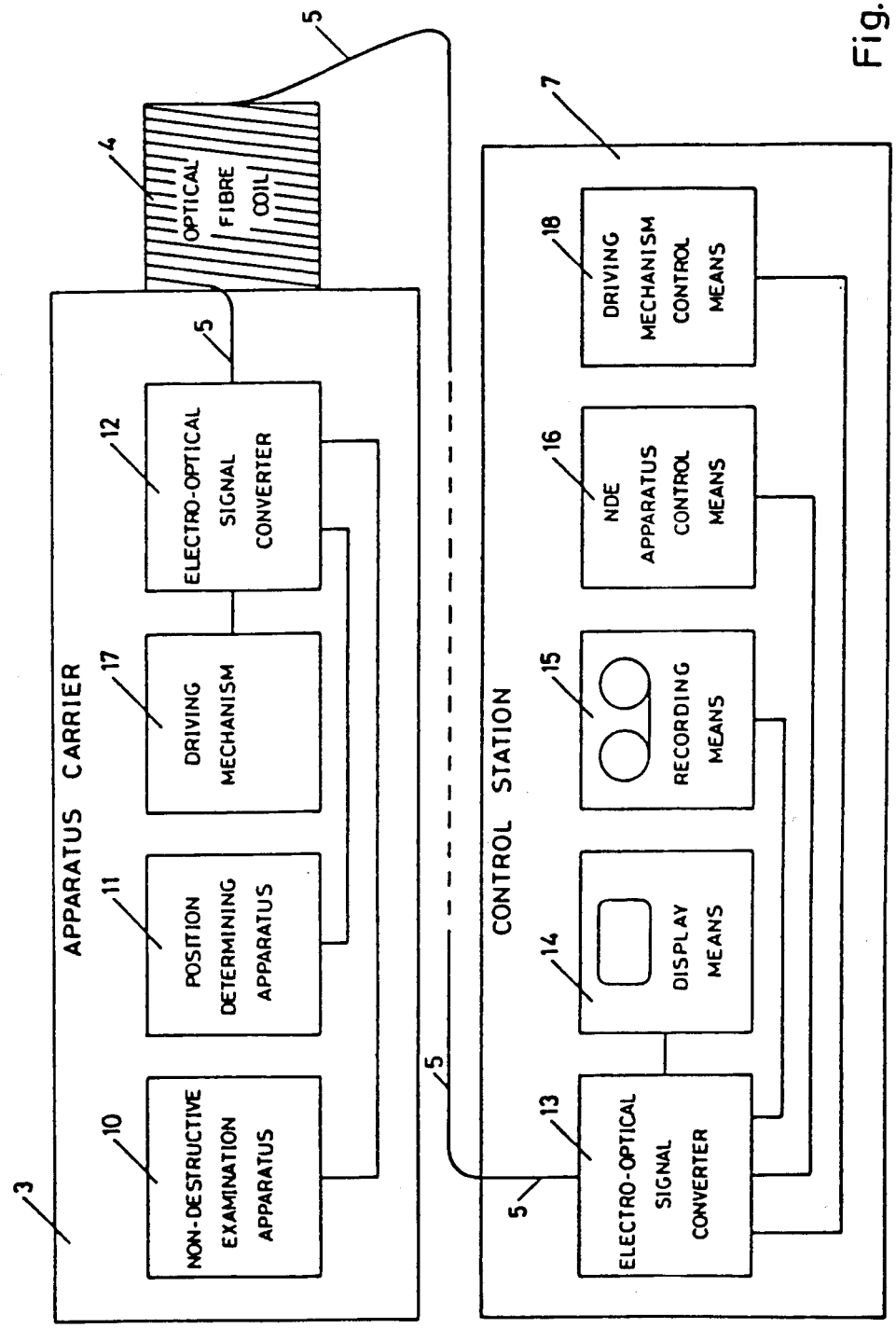
FIG. 2 is a schematic block diagram illustrating the components of an embodiment of the invented system including a self-propelled apparatus carrier.

FIG. 2 shows schematically in more detail the components of the apparatus carrier 3 and the control station 7. The apparatus carrier 3 contains non-destructive examination apparatus 10 adapted to generate electronic measurement signals representative of the successive conditions of the pipeline wall material and surfaces. The apparatus carrier 3 further contains position determining apparatus 11 adapted to generate electronic position signals representative of the successive positions of the carrier during its course of travel. The electronic measurement and position signals are transmitted to a first electro-optical signal converter 12 installed in the apparatus carrier 3 and adapted to convert the electronic signals into corresponding optical signals which are then transmitted through the optical fiber 5 to a second electro-optical signal converter 13 installed in the outside control station 7 and adapted to convert said optical signals back into equivalent electronic measurement and position signals. These latter electronic signals are then transmitted to display means 14 for generating visual displays of the results of the examinations, and to recording means 15 for producing permanent records of the results of the inspection of the pipeline.

The control station 7 further contains first control means 16 adapted to generate electronic control signals for controlling the functions of the non-destructive examination apparatus 10, and adapted to transmit the control signals to the second electro-optical signal converter 13. The signal converter 13 is further adapted to convert said electronic control signals into corresponding optical signals which are then transmitted through the optical fiber 5 to the first electro-optical signal converter 12 installed in the apparatus carrier 3 and further adapted to convert said optical signals back into equivalent electronic control signals. These latter electronic control signals are then transmitted to the non-destructive examination apparatus 10 which is adapted to have its functions controlled by said electronic control signals.

The apparatus carrier 3 of the embodiment shown is further adapted to be self-propelled by means of a driving mechanism 17. Second control means 18 installed in the outside control station 7 are adapted to generate electronic control signals for controlling the function of the driving mechanism 17, and to transmit the control signals to the second electro-optical signal converter 13. The second signal converter 13 is further adapted to convert said electronic control signals into corresponding optical signals which are then transmitted through the optical fiber 5 to the first electro-optical signal converter 12 installed in the apparatus carrier 3 which is further adapted to convert said optical control signals back into equivalent electronic control signals. These latter electronic control signals are then transmitted to the driving mechanism 17 to have its functions controlled by said electronic control signals.

The apparatus carrier 3 may, in principle, be of any kind among the greatly variety of such carriers, pressure-driven or self-propelled, which are known and used in the art. Provided, of course, that the carrier 3 is constructed to enable installing the first electro-optical signal converter 12 and to mount the optical fiber coil 4. Typically, such apparatus carriers may consist of a number of pressure-tight capsules containing the different kinds of apparatus and mechanisms to be carried through the pipeline.

The coil 4 of optical fiber 5 may be an open coil, from the inside or outside of which the fiber is freely and gradually unrolled or uncoiled and deposited inside the pipeline during progressive movement of the apparatus carrier 3 through the pipeline. Also, the coil may be supplemented by any readily apparent dispensing means fulfilling the same purpose. In some instances it may be considered practical to use two or more coils 4 of optical fibers 5 working in parallel, each for its own signal transmission purposes.

The optical fiber 5 may be of any kind known and used in the art for the transmission of optical signals, provided that the optical fiber can be considered expendable in the great lengths normally required and that the fibers can be discarded inside the pipeline or readily removed after the inspection process is completed by a routine cleaning operation without any harmful effects to the normal functioning of the pipeline system. Given these conditions, the fibers may be designed or coated to have sufficient strength and corrosion resistance etc. to function inside the pipeline under the duration of the inspection procedure. In the case of very long pipeline sections it may be necessary to insert one or more miniaturized, battery driven signal regenerators between continuous lengths of optical fiber in order to ensure safe long-distance transmission of the optical signals.

The bushing 8 for receiving the lead-in plug 9 makes it possible to perform the inspection without interruption of the transportation of fluid through the pipeline, provided that the brushing 8 is fitted into the launching trap normally used under these circumstances for the insertion of inspection apparatus carriers and cleaning brushes to be passed through the pipeline. The bushing 8 and the lead-in plug 9 may be designed in several ways readily apparent to those skilled in the art of designing high-pressure components. As an example, the optical fiber may be embedded in a prefabricated glass bar forming the plug 9 fitting into bushing 8.

The non-destructive examination apparatus 10 may be of any kind known and used in the art, provided that the apparatus is able to sense characteristic properties representative of the safety conditions of the pipeline wall material or surfaces, and provided that the apparatus is able to generate corresponding electronic measurement signals representative of these properties. Typical examples of non-destructive examination methods that have been used or may be used for this purpose are remote television with artificial illumination, pressure or vacuum leak testing, ultrasonic examination in all known forms, magnetic flux leakage measurements, and electric measurements such as eddy current examination or corrosion potential measurements. Further examples, some of which may be used in conjunction with television and artificial illumination, are magnetographic and magnetic particle or capillary penetrant examinations, hardness testing and chemical surface analyses.

The position determining apparatus 11 may be of any kind known and used in the state of the art, provided that the step by step position of the apparatus carrier 3 is transformed into corresponding electronic position signals. Typical examples of the position determining principles that have been used for this purpose are the counting of circumferential welds or magnetic markers embedded in the pipeline insulation at known intervals, or revolution counting in connection with the driving mechanisms of self-propelled apparatus carriers. According to the present invention it may further be possible to use the length of optical fiber 5 deposited inside the pipeline as an indicator of the step by step position of the apparatus carrier 3.

The non-destructive examination apparatus 10 and the position determining apparatus 11 may be energized by electric batteries installed in the apparatus carrier or, in the case of in-service inspections, by a turbo-generator mechanism activated by the motion of the fluid in the pipeline as described in the above-mentioned Scherbatskoy U.S. Pat. No. 2,940,302.

The driving mechanism 17 may be of any kind known and used for this purpose in the art, provided that the functions of the driving mechanism can be controlled by appropriate electronic control signals. The driving mechanism may be energized by electric batteries installed in the apparatus carrier 3 or by turbo-generator mechanism activated by the motion of the fluid in the pipeline. The motion of the apparatus carrier may then be brought about by wheels or caterpillar treads in contact with the internal surface of the pipeline.

The first and second electro-optical signal converters 12 and 13 may be of any kind known and used in the art of fiber-optical signal transmission. Single converters may be used, provided that they are able to convert electronic measurement signals into optical signals as well as optical control signals into electronic signals. If it is considered practical to use two or more optical fibers 5 working in parallel, a corresponding number of electro-optical signal converters 12 and 13 will be installed in the apparatus carrier 3 and in the outside control station 7, respectively.

The display means 14 may be of any kind known and used in the art in conjuction with the types of non-destructive examinaton apparatus 10 and position determining apparatus 11 employed, provided that display means 14 is able to generate on-line displays in the form of monitor screen images representative of the step-by-step measurements performed. Typical examples of such display means, able to generate complete projection images of the results of ultrasonic examinations on a television monitor screen, have been described in Lund et al. U.S. Pat. Nos. 3,939,697 and 4,226,122.

The recording means 15 may similarly be of any kind known and used in the art in conjuction with the particular non-destructive examination and position determining apparatus 10 and 11, respectively, employed, provided that recording means 15 is able to produce permanent records of the step-by-step measurements performed, preferably in such a manner that it becomes possible at any later time to recreate monitor screen images of the results of the examinations. A great variety of computerized non-destructive examination systems utilizing permanent storage of measurement data on magnetic tapes or disks will satisfy these provisions. A typical example of such recording means is the computerized ultrasonic examination system described in the above-mentioned Lund et al. U.S. Pat. No. 4,226,122.

Finally, the non-destructive examination apparatus control means 16 and driving mechanism control means 18 may similarly be of any kind known and used in the art, provided that they are able to generate the appropriate electronic control signals for controlling the functions of the particular apparatus 10 and mechanism 17 employed. Preferably, the display, recording and control means 14, 15, 16 and 18 of the outside control station 7 can be combined into one integrated, computerized and keyboard controlled electronic data processing system.

An extensive description of a fully computerized data processing system of this kind, including automatic remote control by electonic signals of the functions of an ultrasonic examination apparatus, and automatic remote control of the functions of a driving mechanism for the positioning and exchange of ultrasonic sensor probes, has been given in Beller U.S. Pat. No. 3,857,052, citing Appelton U.S. Pat. No. 3,259,021, directed to methods and apparatus for performing remote controlled in-service inspection of atomic reactors and the like.

It will be understood that several modifications and variations of the system may be effected without departing from the spirit and scope of the novel concepts of the present invention.

I claim:
1. A system for the internal inspection of a pipeline for carrying fluids, such as oil or gas, comprising:
   an apparatus carrier to be inserted in the pipeline and travel inside the pipeline from point to point over considerable distances of several kilometers;
   non-destructive examination apparatus mounted in said apparatus carrier to generate electronic measurement signals representative of at least one of the conditions of the pipeline wall material and surfaces;
   position determining apparatus mounted in said apparatus carrier to generate electronic position representative of the successive positions of said apparatus carrier during said travel;
   at least one first electro-optical signal converter installed in said apparatus carrier, said first electro-optical signal converter being connected to convert said electronic measurement signals and said electronic position signals into corresponding optical signals;

at least one second electro-optical signal converter situated outside a carrier launching end of the pipeline, said second electro-optical signal converter being connected to convert said optical signals into equivalent electronic signals;

at least one coil of expendable, thin optical fiber consisting of a single naked strand without supporting mantle having a length of several kilometers to be at least the same length as the pipeline section to be examined, said coil being mounted on said apparatus carrier to gradually deposit said optical fiber inside said pipeline during said travel of said apparatus carrier, said optical fiber to remain in said pipeline after the internal inspection, said optical fiber being connected to transmit optical signals between said first electro-optical signal converter and said second electro-optical signal converter situated outside said carrier launching end of the pipeline; and display and recording means situated outside said carrier launching end of the pipeline, said display and recording means being connected with said second electro-optical signal converter to receive said electronic signals and thereby generate displays and permanent recordings of the results of the inspection of the pipeline.

2. The combination of claim 1 wherein:

said non-destructive examination apparatus is constructed to have its functions controlled by means of appropriate electronic control signals;

said first electro-optical signal converter is connected to convert optical signals into equivalent electronic control signals for controlling the functions of said non-destructive examination apparatus;

said second electro-optical signal converter is connected to convert electronic control signals into corresponding optical control signals; and first control means situated outside said carrier launching end of the pipeline is connected with said second electro-optical signal converter to generate and transmit appropriate control signals for controlling the functions of said non-destructive examination apparatus in said apparatus carrier.

3. The combination of claim 2 wherein:

said apparatus carrier is constructed to be self-propelled by means of a driving mechanism, said driving mechanism being connected to have its functions controlled by means of appropriate electronic control signals; and said driving mechanism is connected through said first electro-optical signal converter, said optical fiber, and said second electro-optical signal converter with second control means situated outside said carrier launching end of the pipeline, said second control means being constructed to generate and transmit appropriate electronic control signals for controlling the functions of said driving mechanism in said apparatus carrier.

4. The combination of claim 1 wherein:

said apparatus carrier is constructed to be self-propelled by means of a driving mechanism, said driving mechanism being connected to have its functions controlled by means of appropriate electronic control signals; and said driving mechanism is connected through said first electro-optical signal converter, said optical fiber, and said second electro-optical signal converter with second control means situated outside said carrier launching end of the pipeline, said second control means being constructed to generate and transmit appropriate electronic control signals for controlling the functions of said driving mechanism in said apparatus carrier.

* * * * *